(12) United States Patent
Poetter et al.

(10) Patent No.: US 8,034,911 B2
(45) Date of Patent: Oct. 11, 2011

(54) NUCLEIC ACID ANCHORING SYSTEM COMPRISING COVALENT LINKAGE OF AN OLIGONUCLEOTIDE TO A SOLID SUPPORT

(75) Inventors: Karl Frederick Poetter, Northcote (AU); Brendan James Toohey, Clifton Hill (AU)

(73) Assignee: Genera Biosystems Limited, Bundoora (AU)

( * ) Notice: Subject to any disclaimer, the term of this patent is extended or adjusted under 35 U.S.C. 154(b) by 0 days.

(21) Appl. No.: 12/821,009

(22) Filed: Jun. 22, 2010

(65) Prior Publication Data

US 2010/0261891 A1 Oct. 14, 2010

Related U.S. Application Data

(63) Continuation of application No. 10/517,003, filed as application No. PCT/AU03/00696 on Jun. 4, 2003, now Pat. No. 7,741,459.

(30) Foreign Application Priority Data

Jun. 4, 2002 (AU) .................................. PS2764/02

(51) Int. Cl.
C07H 21/00 (2006.01)
C07H 21/02 (2006.01)
C12Q 1/68 (2006.01)
G01N 33/00 (2006.01)

(52) U.S. Cl. .......... 536/23.1; 536/24.3; 435/6; 435/7.92
(58) Field of Classification Search .................. 536/23.1, 536/24.3; 435/6, 7.92
See application file for complete search history.

(56) References Cited

U.S. PATENT DOCUMENTS

| 6,030,782 | A | 2/2000 | Anderson et al. |
| 6,812,334 | B1 | 11/2004 | Mirkin et al. |
| 6,858,711 | B2 | 2/2005 | McGall et al. |

FOREIGN PATENT DOCUMENTS

WO 0148244 A2 7/2001

OTHER PUBLICATIONS

Rogers et al., "Immobilization of Oligonucleotides Onto a Glass Support via Disulfide Bonds: A Method for Preparation of DNA Microarrays" Anal. Biochem. 266(1): 23-30, Jan. 1, 1999.
Zhang et al., "Single-base Mutational Analysis of Cancer and Genetic Diseases Using Membrane Bound Modified Oligonucleotides" Nucleic Acids Res. 19(14): 3929-3933, Jul. 25, 1991.

*Primary Examiner* — Jezia Riley
(74) *Attorney, Agent, or Firm* — SEED IP Law Group PLLC

(57) ABSTRACT

The anchoring system generally comprises a solid support and a chemical linking moiety useful for ether formation with another chemical moiety on a nucleic acid molecule. The present invention further contemplates methods for anchoring a nucleic acid molecule to a solid support via a covalent linkage. The anchoring system of the present invention is useful inter alia in construction of nucleic acid arrays, to purify nucleic acid molecules and to anchor nucleic acid molecules so that they can be used as templates for in vitro transcription and/or translation experiments and to participate in amplification reactions. The present invention is particularly adaptable for use with microspheres and the preparation of microsphere suspension arrays and optical fiber arrays. The anchoring system permits the generation of an anchored oligonucleotide for use as a universal nucleic acid conjugation substrate for any nucleic acid molecule or population of nucleic acid molecules. The present invention further provides a kit useful for anchoring nucleic acid molecules or comprising nucleic acid molecules already anchored to a solid support.

9 Claims, 10 Drawing Sheets

| Linker Component | Representation in diagrams |
|---|---|

Acrydite (Acryl) group

Spacer

Tag DNA Sequence; RNA polymerase promoter + transcription/translation start signals

Complete Tag Linker

Figure 3A Tag Sequence   5'-ATTTAGGTGACACTATAGA-OH-3'
|||||||||||||||
Figure 3B α-Tag Sequence  3'-FAM-TAAATCCACTGTG-PO₄-5' a. A 187 bp DNA fragment generated by PCR with the following landmarks:

Forward Primer (phosphorylated)
Complement (Cy5 labelled) on reverse strand to the forward Primer
Reverse Primer (FAM labelled)
Sequence on Forward strand complementary to Reverse primer
Internal Sequence on forward strand
Sequence on Reverse strand (FAM labelled) complementary to ▬▬

NUCLEIC ACID ANCHORING SYSTEM COMPRISING COVALENT LINKAGE OF AN OLIGONUCLEOTIDE TO A SOLID SUPPORT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 940120_402C1_SEQUENCE_LISTING.txt. The text file is 3 KB, was created on Jun. 22, 2010, and is being submitted electronically via EFS-Web.

BACKGROUND OF THE INVENTION

1. Field of the Invention

The present invention relates generally to an anchoring system for nucleic acid molecules. The anchoring system generally comprises a solid support and a chemical linking moiety useful for ether formation with another chemical moiety on a nucleic acid molecule. The present invention further contemplates methods for anchoring a nucleic acid molecule to a solid support via a covalent linkage. The anchoring system of the present invention is useful inter alia in construction of nucleic acid arrays, to purify nucleic acid molecules and to anchor nucleic acid molecules so that they can be used as templates for in vitro transcription and/or translation experiments and to participate in amplification reactions. The present invention is particularly adaptable for use with microspheres and the preparation of microsphere suspension arrays and optical fiber arrays. The anchoring system permits the generation of an anchored oligonucleotide for use as a universal nucleic acid conjugation substrate for any nucleic acid molecule or population of nucleic acid molecules. The present invention further provides a kit useful for anchoring nucleic acid molecules or comprising nucleic acid molecules already anchored to a solid support.

2. Description of the Prior Art

Reference to any prior art in this specification is not, and should not be taken as, an acknowledgment or any form of suggestion that this prior art forms part of the common general knowledge in any country.

The increasing sophistication of recombinant DNA technology is greatly facilitating research and development in a range of biotechnology-related industries.

Many manipulations involving nucleic acid molecules require immobilization strategies. One immobilization strategy involves the use of binding partners such as avidin and streptavidin. Whilst the latter system has been successfully employed in many nucleic acid anchoring systems, it does have some limitations and does not enable the full gamut of nucleic acid manipulations now available to be performed on single and mixtures of nucleic acid molecules. It is also subject to non-specific binding thus limiting the accuracy of any immobilization reactions.

In addition, there are difficulties in using linker systems like streptavidin and avidin in automated and high throughput systems.

The immobilization procedure can be complex and involve the use of expensive reagents. There is a need, therefore, to develop a universal conjugation system for nucleic acid molecules.

In accordance with the present invention, a universal conjugation system has been developed for anchoring nucleic acid molecules to a solid support. The system of the present invention has a myriad of uses in molecular biology including micro or macro nucleic acid arrays, capturing, purifying and/or sorting nucleic acid molecules, RNA production for RNAi and short, interfering RNA (si-RNA) applications and microsphere nucleic acid technology, especially for microengineered structures and nanoshells. The system may also be usefully employed in high throughput and/or automated systems. In particular, the present invention provides a re-usable anchoring system for nucleic acid molecules.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides a conjugation system for target nucleic acid molecules. The conjugation system facilitates immobilization or anchoring of the target nucleic acid molecules to a solid phase. The solid phase may be any form of solid support including microspheres, microchips, beads, slides such as glass slides, microliter wells and dipsticks amongst many others.

The solid support is generally selected on the basis of ease of manipulation, inexpensiveness, thermal stability and stability to aqueous and/or organic solvents.

Silica and methacrylate microspheres are particularly useful especially for use in suspension arrays or optical fiber arrays.

The solid support is generally modified to include a chemical moiety capable of engaging in the formation of a covalent bond with another chemical moiety present on a nucleic acid molecule (the tag oligonucleotide). Any number of chemical moieties may be employed on the solid support but in a preferred embodiment, the solid support comprises a thiolated surface capable of engaging in covalent bond formation with an acryl group linked to the 5' end of a tag oligonucleotide via a spacer between the 5' base of the oligonucleotide and the active group. One preferred form of anchoring system is shown in FIG. 1.

The level of success in anchoring the tag oligonucleotide to the solid support is measured by annealing an oligonucleotide which is complementary to the tag oligonucleotide (referred to herein as the "α-tag") optionally labeled with a reporter molecule such as but not limited to 6-FAM. The annealing of the α-tag results, in a preferred embodiment, in a 3' single-stranded overhang (or "sticky end") comprising the tag oligonucleotide.

Any target nucleic acid molecule is then ligated to the tag oligonucleotide via a bridging oligonucleotide. The bridging oligonucleotide comprises a sequence of nucleotides complementary to a nucleotide sequence of the 3' overhang portion of the tag oligonucleotide and a sequence of oligonucleotides complementary to a 5' end portion of a target nucleic acid molecule.

Accordingly, a target nucleic acid conjugating system is provided comprising a solid support having a tag oligonucleotide covalently bound to the surface of the solid support, the tag oligonucleotide rendered partially double-stranded by annealing an α-tag oligonucleotide to the tag oligonucleotide to provide a 3' overhang single-stranded portion of the tag oligonucleotide to which is annealed a bridging oligonucleotide having a nucleotide sequence capable of hybridizing to the 5' end portion of a target nucleic acid molecule. Conveniently, the bridging oligo is removed from the support prior to becoming active.

In one embodiment, therefore, the present invention provides a universal nucleic acid anchoring system comprising the structure:—

$$S(-T)_p$$

wherein:
S is a solid support having a chemical moiety capable of covalent bond formation with a second chemical moiety;
T is a tag oligonucleotide comprising single-stranded DNA having said second chemical moiety linked via a spacer molecule to its 5' end, said spacer comprising mc+n atoms, having from about 1 to about 100 atoms, where m is the number of repeats of a small subunit, c is the number of atoms in each repeat, and n is the number of atoms not in the repeat; said T further comprising a bridging oligonucleotide having a nucleotide sequence complementary to 3' overhang nucleotides on the tag oligonucleotide and a further nucleotide sequence complementary to a nucleotide sequence on a 5' end of a target nucleic acid molecule;
wherein T may be represented p times on the solid support wherein p is from about 1 to about 100,000.

In the above structure, the line "-" represents a covalent bond between a solid support surface chemical moiety and the chemical moiety on the tag oligonucleotide.

The universal anchoring system of the present invention permits the generation of arrays of nucleic acid molecules. When the solid support comprises microspheres, the present invention permits the generation of suspension arrays. The anchored nucleic acid molecules may be subject to, for example, mutation identification or other manipulations such as in vitro transcription and/or translation reactions.

The nucleic acid anchoring system, i.e. $S(-T)_p$, may be re-used and, hence, only a single anchoring reaction need take place for virtually unlimited customizations via specific targets and bridges The present invention further contemplates a method for anchoring a target nucleic acid to a substrate, said substrate comprising:—
(i) a solid support having a surface chemical moiety;
(ii) a tag oligonucleotide having a chemical moiety linked to its 5' end via a spacer comprising a molecule with mc+n atoms wherein m is the number of repeats of a small subunit and c is the number of atoms in each repeat and n is the number of atoms not in the repeat wherein the latter chemical moiety is in covalent bond formation with the chemical moiety on the surface of the solid support;
(iii) a complementary (α) tag oligonucleotide sequence which has hybridized to said tag oligonucleotide sequence such that there is a single-stranded nucleotide sequence constituting a 3' overhang of the tag oligonucleotide;
(iv) a bridging oligonucleotide having a complementary nucleotide sequence to the nucleotide sequence of the 3' overhang portion of the tag oligonucleotide and which bridging oligonucleotide has hybridized to its complementary sequence on the tag oligonucleotide leaving a single-stranded portion of the bridging oligonucleotide which has a complementary nucleotide sequence to the 5' terminal portion of said target nucleic acid molecule;

wherein said method comprises contacting said target nucleic acid molecule to said substrate for a time and under conditions to permit hybridization of the 5' portion of the nucleic acid molecule to the single-stranded portion of the bridging oligonucleotide and permitting ligase-mediated covalent bond formation between said target nucleic acid molecule and the substrate.

A spacer generally but not necessarily comprise carbon and oxygen based molecules or is a hydrocarbon molecule such as having from about 1 to about 100 atoms, more preferably from about 18 to about 50 atoms and even more preferably from about 24 to about 36 atoms is particularly useful.

The spacer molecule is conveniently an alkyl, alkenyl or an alkynyl molecule including a hydrocarbon molecule. Preferably, the spacer is a linear non-branched hydrocarbon although many other molecules may be employed such as ethylene oxy (PEG) or one or more amino acids to separate the oligonucleotide from the surface of the solid support as long as they are inert in terms of the constructs intended application.

A summary of sequence identifiers used throughout the subject specification is provided in Table 1.

TABLE 1

Summary of sequence identifiers

| SEQUENCE ID NO: | DESCRIPTION |
|---|---|
| 1 | nucleotide sequence of 5'-acrydite universal tag |
| 2 | nucleotide sequence of PO4 complementary tag |
| 3 | nucleotide sequence of bridge oligonucleotide |
| 4 | nucleotide sequence of PO4 target |
| 5 | nucleotide sequence of a target synthesized with 5' PO4 |
| 6 | nucleotide sequence of a terminal T3 polymerase signal sequence |
| 7 | nucleotide sequence of target DNA sequence |
| 8 | nucleotide sequence of 5' overhang of common sequence of bridge |
| 9 | nucleotide sequence of common sequence of bridge |
| 10 | nucleotide sequence of a tag sequence (FIG. 3A) |
| 11 | nucleotide sequence of an α-tag sequence (FIG. 3B) |

A list of terms used herein is provided in Table 2.

TABLE 2

Terms

| TERM | DESCRPTION |
|---|---|
| tag oligonucleotide or tag | oligonucleotide molecule anchored to a solid support face via a covalent bond between a chemical moiety on the surface of the solid support and a chemical moiety conjugated to the oligonucleotide via a spacer molecule |
| α-tag | oligonucleotide molecule comprising a nucleotide sequence complementary to the tag oligonucleotide sequence |
| solid support | form of solid phase; includes microspheres, microchips, beads and slides |
| bridging oligonucleotide | oligonucleotide which bridges the tag oligonucleotide and the target nucleic acid molecule; the bridging oligonucleotide has a nucleotide sequence complementary to a 3' nucleotide sequence on tag and an end portion of the target nucleic acid molecule |
| spacer | a molecule comprising a number of atoms and having the structure mc + n wherein m is the number of repeats, and c is the number of atoms in each repeat and n is the number of atoms not in the repeat |

TABLE 2-continued

Terms

| TERM | DESCRPTION |
|---|---|
| target nucleic acid molecule | DNA or RNA target having a single-stranded end portion complementary to part of the bridging oligonucleotide |
| anchoring/anchored | joining of two molecules via a covalent linkage |
| chemical moiety | a chemical group capable of forming a covalent bond with another chemical moiety |

BRIEF DESCRIPTION OF THE FIGURES

FIG. 7 is a graphical representation showing universal binding analogs for general use bridges in ligation-mediated conjugation of tagged microspheres. All bridges had a common sequence of 5'-CXXXXXT [SEQ ID NO:8] CAT AGC TGT CCT-3' [SEQ ID NO:9]. The 3' italicized 12 bases were common to, all bridges and hybridized to the 3' 12 bases of the immobilized tag. The underlined sequence CXXXXXT [SEQ ID NO:8} represents the variable 5' overhang which hybridized to the target sequence. The Xs represent nucleotide positions which were variable in this test between the actual base and inosines, which are general binding base analogs.

DETAILED DESCRIPTION OF THE INVENTION

Figure 1A:
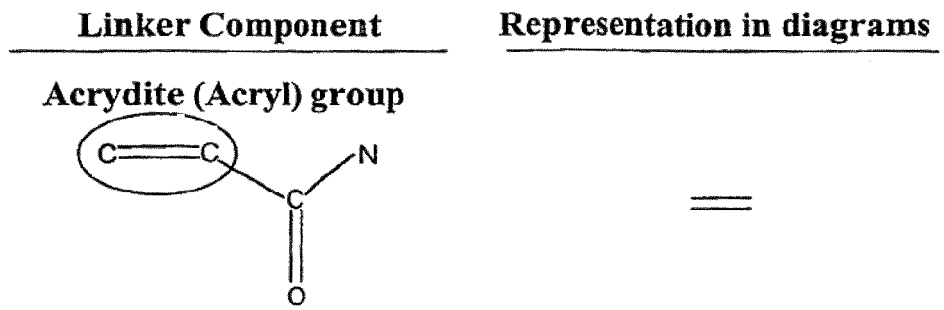
FIG. 1 is a diagrammatic representation of the three component linker used to modify thiolated solid phase, especially silica microsphere activated by silanization with 3-mercaptopropyl trimethoxysilane. AU components are synthesized using standard phosphoramidite coupling chemistry. (A) Reactive group; (B) Spacer (18 atom spacer, with m=6; c=3 and n=2 following designation of mc+n atoms in the spacer; (C) Tag DNA sequence. This component is variable and can be engineered for specific application; (D) Complete Tag Linker. This component serves the purpose of separating the DNA of interest (referred to as Target DNA in text) from the surface as well as provides a method for amplification of Target after molecular testing.
Figure 1B:
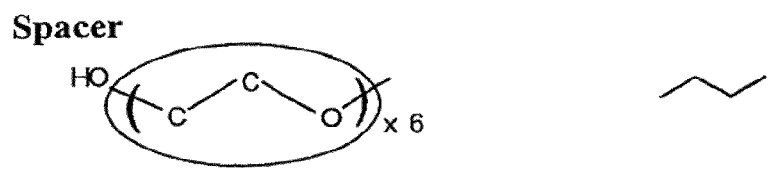
Figure 1C:
Figure 1D:

The present invention provides a nucleic acid anchoring system which facilitates ligase-mediated conjugation of a target nucleic acid molecule to a solid support via a tag oligonucleotide which is conjugated to the solid support via a covalent bond between a chemical moiety resident on the solid support and another chemical moiety on the tag nucleic acid molecule.

A first aspect of the present invention, therefore, is a tag oligonucleotide anchored to a solid support.

Accordingly, one aspect of the present invention provides a solid phase comprising a surface with a first chemical moiety capable of participating in covalent bond formation with a second chemical moiety conjugated to a tag oligonucleotide wherein the tag oligonucleotide is a substrate for ligase-mediated covalent bonding to a target nucleic acid molecule.

In one embodiment, the chemical moiety on the surface of the solid phase is capable of covalent bond formation with a tag-associated amine group, thiol group or acryl group.

Accordingly, another aspect of the present invention is directed to a solid phase comprising a surface with a first chemical moiety selected from a carboxyl group, an amine group, and a thiol group, said first chemical moiety capable of participating in covalent bond formation with a second chemical moiety selected from an amine group, a thiol group and an acryl group conjugated to an oligonucleotide with the proviso that when the solid phase surface moiety is a carboxyl group then the covalent bond forms with an amine group, when the surface moiety is a thiol group the tag associated moiety is an acryl group or thiol group, or amine group linked via a heterobifunctional linker. The present invention extends, however, to chemical moieties capable of any form of covalent bond formation with any other chemical entity.

In one preferred embodiment, the chemical moiety on the surface of the solid phase is a carboxyl group and such a group is capable of covalent bond formation with a number of chemical moieties but especially an amine group and when the solid phase chemical moiety is an amine group or a thiol group several methods employing heterobifunctional crosslinkers allow covalent bond formation with an aminated or thiolated tag oligonucleotide.

Accordingly, another aspect of the present invention is directed to a solid phase comprising either a surface carboxyl group capable of participating in covalent bond formation with an amine group, or a surface encoded amine or thiol group conjugated to a tag oligonucleotide via a crosslinker.

In a most preferred embodiment, the solid phase surface chemical moiety is a thiol group.

Most preferably, the chemical moiety conjugated to the tag oligonucleotide is an acryl group.

In this embodiment of the present invention, there is provided a solid phase comprising a surface thiol group capable of participating in covalent bond formation with an acryl group conjugated to a tag oligonucleotide.

The solid phase is preferably in the form of a solid support such as a microsphere, bead, glass, ceramic or plastic slide, a dipstick or the wall of a vessel such as a microtiter well. The form of the solid support is not critical and may vary depending on the application intended. However, microspheres such as silica or methacrylate microspheres are particularly useful in the practice of the present invention, especially for use in suspension arrays or optical fiber arrays.

The selection of solid supports is conveniently based on ease of manipulation, level of expense, thermal stability and/or stability in aqueous and/or organic solvents.

In a particularly preferred embodiment, therefore, the present invention is directed to microspheres having a thiolated surface capable of participating in linker mediated or direct covalent bond formation with a chemical moiety selected from an amine group, a thiol group and an acryl group conjugated to a tag oligonucleotide.

Generally, any number of chemical moieties may be present or exposed on the surface of the solid support and these may range from a few hundred to several thousand.

In a particularly preferred embodiment, there are from about 1 to about 100,000 surface chemical moieties potentially involved in covalent bonding per solid support. This is particularly the case when the solid support is a microsphere. Conveniently, the microsphere comprises from about 500 to about 80000 or more conveniently from about 1000 to about 80000 chemical moieties per bead. Examples include 1000, 2000, 3000, 4000, 5000, 6000, 7000, 8000, 9000, 10000, 11000, 12000, 13000, 14000, 15000, 16000, 17000, 18000, 19000, 20000, 21000, 22000, 23000, 24000, 25000, 26000, 27000, 28000, 29000, 30000, 31000, 32000, 33000, 34000, 35000, 36000, 37000, 38000, 39000, 40000, 41000, 42000, 43000, 44000, 45000, 46000, 47000, 48000, 49000, 50000, 51000, 52000, 53000, 54000, 55000, 56000, 57000, 58000, 59000, 60000, 61000, 62000, 63000, 64000, 65000, 66000, 67000, 68000, 69000, 70000, 71000, 72000, 73000, 74000, 75000, 76000, 77000, 78000, 79000 or 80000.

In relation to one preferred embodiment, therefore, the present invention provides microspheres each comprising from about 3000 to about 80000 such as about 4000 to about 80000 or more particularly about 50000 to about 80000 surface thiol groups per microsphere.

The tag oligonucleotide having the chemical moiety capable of covalent bond formation with the solid phase surface chemical moiety may comprise any nucleotide sequence although the nucleotide sequence would generally be known. One particularly useful sequence is an RNA polymerase promoter nucleotide sequence such as the T3 RNA polymerase promoter nucleotide sequence. The benefit of the latter in terms of linking DNA is the ability to generate RNA transcripts. However, any oligonucleotide of known sequence may be employed. The term "oligonucleotide" is not to be viewed to any limiting extent and may comprise from about 10 base pairs (bp) to hundreds of bp.

It is convenient to ensure that after binding of the tag oligonucleotide to the solid phase that the tag oligonucleotide does not exhibit interference with the solid support surface. Consequently, a spacer molecule is generally included between the chemical moiety and the 5' end of the tag oligonucleotide. A spacer generally but not necessarily comprise carbon and oxygen based molecules or is a hydrocarbon molecule such as having from about 1 to about 100 atoms, more preferably from about 18 to about 50 atoms and even more preferably from about 24 to about 36 atoms is particularly useful. Examples of the number of atoms in the spacer include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100.

The spacer may also be multiple repeats such as 2×(18 atoms) spacers or 3×(6 atoms) spacers. The length of the spacer is not critical for most applications as long as a crucial distance threshold between the bead surface and the active end of the DNA tag is maintained.

Consequently, another aspect of the present invention contemplates an isolated tag oligonucleotide comprising a chemical moiety capable of covalent bond formation with a chemical moiety on the surface of a solid phase, said first mentioned chemical moiety conjugated to said tag oligonucleotide via a spacer molecule having mc+n atoms wherein m is the number of repeats, c is the length of the repeat and n is the number of atoms of the spacer molecule not contained in repeats.

Generally, m is from about 1 to about 12 such as 1, 2, 3, 4, 5, 6, 7, 8, 9, 10, 11 or 12 and n is preferably 1 or from 0 to about 10 such as 0, 1, 2, 3, 4, 5, 6, 7, 8, 9 or 10.

Conveniently, mc+n is from about 1 to about 100 such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100. Advantageously, the atoms are carbon or oxygen atoms.

The spacer molecule is conveniently an alkyl, alkenyl or an alkynyl molecule including a hydrocarbon molecule. Preferably, the spacer is a linear non-branched hydrocarbon although many other molecules may be employed such as ethylene oxy (PEG) or one or more amino acids to separate the oligonucleotide from the surface of the solid support as long as they are inert in terms of the constructs intended application.

The 5' tag oligonucleotide chemical moiety is conveniently an amine group, a thiol group or an acryl group if the solid support surface chemical moiety is a thiol group.

In a most preferred embodiment, the 5' chemical moiety on the tag oligonucleotide is an acryl group.

In accordance with the above aspect of the present invention, the solid support is preferably a microsphere although any solid support may be employed.

Accordingly, another aspect of the present invention provides a solid phase comprising a tag oligonucleotide anchored to the surface of said solid phase via a covalent bond between a chemical moiety on the surface of the solid phase and a chemical moiety conjugated to said tag oligonucleotide via a multi atom spacer having the structure mc+n wherein m is the number of repeats, c is the size of the repeat, and n is the number of atoms not included in the repeats.

As indicated above, mc+n is from about 1 to about 100.

As indicated above, the covalent bond is conveniently a thiol group covalently bonded to an acryl group or covalently bridged through bifunctional linkers to tag encoded amines or thiols. Furthermore, the spacer molecule is preferably from about 1 to about 100 carbon atoms in length.

Consequently, another aspect of the present invention comprises an article of manufacture having the structure:—

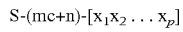

$$S\text{-}(mc+n)\text{-}[x_1 x_2 \ldots x_p]$$

wherein:
S is a solid support;
m is the number of repeats;
c is a repeat of size c;
n is the number of atoms not included in repeats; and
$[x_1 x_2 \ldots x_p]$ is a nucleotide sequence of nucleotides $x_1 x_2 \ldots x_p$ wherein each of $x_1 x_2 \ldots x_p$ may be the same or different and the nucleotide length, p, is from 5 to about 200.

In the above formation, the schematic "-" represents a covalent bond such as, for example, an amide bond or a thioether bond.

The oligonucleotide sequence, i.e. $x_1 x_2 \ldots x_p$ is any known sequence such as the T3 RNA polymerase promoter. The oligonucleotide sequence may also comprise an additional nucleotide sequence having, for example, translation start signals, ribosome binding sites and an initiating methionine (ATG) triplet.

It is particularly convenient to ensure or to measure successful covalent attachment of the tag oligonucleotide sequence to the solid phase. This can be accomplished by incorporating an internal fluor within the tag oligonucleotide sequence. This would give an immediate and simple test of amount of binding. However, this approach is operationally limiting because in most instances, the internal fluor confounds future applications by either interfering with data readout or by interfering by inhibiting the chemistry of the anchored system.

A preferred approach to measurement of amount of conjugated tag oligonucleotide is to prepare a labeled reverse complement to the tag oligonucleotide. Conveniently, the labeled oligonucleotide sequence is complementary to the 5' end of the anchored tag oligonucleotide sequence. The label may be any suitable label such as 6-FAM. The 5' end is generally phosphorylated.

Accordingly, another aspect of the present invention provides a solid phase comprising a tag oligonucleotide of known sequence anchored thereto via a covalent linkage between a chemical moiety on the surface of the solid phase and a chemical moiety conjugated to the tag oligonucleotide via a molecule of mc+n atoms wherein m is the number of repeated atoms, c is the number of atoms in a repeat and n is the number of atoms not in the repeat and wherein mc+n is from about 1 to about 100, said solid phase further comprising a second oligonucleotide sequence annealed by base pairing to a complementary nucleotide sequence on said first mentioned tag oligonucleotides resulting in an overhang at the 3 end of either the tag oligonucleotide or its complementary oligonucleotide.

Preferably, the second oligonucleotide sequence comprises a label and is used to measure the success or otherwise of the covalent anchoring of the first oligonucleotide sequence to the solid phase.

The preferred label is 6-FAM.

Preferably, the first oligonucleotide sequence overhangs at its 3' end over the second oligonucleotide sequence.

As indicated above, the second oligonucleotide is labeled and, hence, it becomes a convenient assay for the success or otherwise of covalent attachment of the first oligonucleotide to the solid phase. One skilled in the art will immediately recognize that there are many variations in order to determine the extent of covalent linkage and that the present invention should not be only limited to one particular means.

The essence of this aspect of the invention is a solid phase having a first tag oligonucleotide attached thereto via covalent linkage between a first chemical moiety on the surface of the solid phase (e.g. a carboxyl group) and a second chemical moiety conjugated to the first oligonucleotide via a spacer molecule of length mc+n atoms as defined above and a second tag oligonucleotide, optionally labeled with a reporter molecule capable of giving an identifiable signal, which anneals to complementary nucleotide sequences on the first oligonucleotide to provide, in a preferred embodiment, a 3' overhang of the first tag oligonucleotide and wherein the 5' end of the second tag oligonucleotide is phosphorylated.

The complementary oligonucleotide to the tag oligonucleotide is referred to herein as α-tag or the α-tag oligonucleotide.

The present invention provides, therefore, in one embodiment:—
(i) a solid phase such as a microsphere, microchip or the sides of a well in a microliter plate; and
(ii) a tag oligonucleotide having a chemical moiety conjugated to the oligonucleotide via a molecule of mc+n atoms as described above;
wherein the chemical moiety on the oligonucleotide is in covalent bond formation with a chemical moiety on the surface of the solid phase.

Again, as stated above, although a covalent linkage such as an amide bond or thioether bond is particularly useful in the practice of the present invention, it is but one of a whole myriad of covalent linkages which may be used in accordance with the present invention.

In general, the efficient production of a solid phase, especially on a surface with great stability, is difficult. In many systems, great care is required to ensure maximally efficient chemical reactions. Enzymatic manipulations, on the other hand, are relatively easy and can be performed in aqueous solutions, at moderate temperatures. The main advantage of the system described here is flexibility. Since the difficult covalent linkage between tag and solid phase is only performed once in a large stock, subsequent additions to the initial tag DNA is done easily at any point in the future with virtually any desired target DNA on whatever portion of the original stock required by a particular application.

The above solid support generally further comprises a second oligonucleotide (α-tag) in complementary base pairing to the first mentioned oligonucleotide (tag) such that there is optionally a label on the 3' end of the α-tag oligonucleotide and the 5' end is phosphorylated wherein the tag oligonucleotide overhangs the α-tag oligonucleotide at the 3' end of the tag oligonucleotide.

The next step is the generation of a bridge oligonucleotide which enables anchoring of a target nucleic acid molecule to the tag oligonucleotide anchored to the solid phase.

The bridging oligonucleotide, in the case where the tag oligonucleotide overhangs at its 3' end relative to the annealed αtag oligonucleotide, anneals in a direction where the bridge's 3" end is reverse complementary to the overhanging portion of the tag oligonucleotide The bridge's 5' end is thus a 5' overhang of the tag: bridge double stranded (ds) DNA.

The 5' end of the bridge is then reverse complementary to the 5' end portion of a target nucleic acid molecule. Both the 5' end of the target nucleic acid molecule and the 5' end of the labeled α-tag oligonucleotide (complementary to the anchored tag oligonucleotide) are phosphorylated. A ligase-mediated covalent attachment then forms anchoring the target nucleic acid molecule to the anchored tag via the bridging oligonucleotide.

Accordingly, in one embodiment, there is provided a substrate for anchoring a target nucleic acid molecule, said substrate comprising:—

(i) a solid phase having a first chemical moiety on its surface;
(ii) a tag oligonucleotide comprising a second chemical moiety in covalent bond formation with the first chemical moiety, said second chemical moiety conjugated to the tag oligonucleotide via a molecule of structure mc+n atoms as defined above;
(iii) an optionally labeled oligonucleotide reverse complementary to the tag oligonucleotide; and
(iv) a bridging oligonucleotide having complementary based to the 3' overhang region of the tag oligonucleotide and complementary bases to the 5' end portion of the target nucleic acid molecule wherein the target nucleic acid molecule is anchored to the tag oligonucleotide via ligase-mediated conjugation.

The bridging oligonucleotide may be part of the solid phase complex prior to anchoring of the target nucleic acid molecule or it may be first added to and annealed to the target nucleic acid molecule prior to annealing to the tag oligonucleotide.

Yet in a further embodiment, the solid phase-tag oligonucleotide complex, the bridging oligonucleotide and the target nucleic acid molecule are mixed together and subjected to ligation conditions.

The target nucleic acid molecule is specific for each conjugation experiment. Generally, its initial 5-30 bases are complementary to the bases at the 5' end of the bridging oligonucleotide. The 5' end of the target nucleic acid molecule is generally phosphorylated. A minimum of five bases complementary between the target nucleic acid molecule and the tag oligonucleotide is enough to enable ligation but generally insufficient to permit cross-hybridization, especially when multiplexing a large number of target molecules.

Yet another aspect of the present invention provides a universal nucleic acid anchoring system comprising the structure:—

$$S(-T)_p$$

wherein:

S is a solid support having a chemical moiety capable of covalent bond formation with a second chemical moiety;

T is a partially double-stranded oligonucleotide comprising single-stranded tag oligonucleotide having said second chemical moiety linked via a spacer molecule to its 5' end, said spacer comprising carbon atoms having the structure mc+n wherein in is the number of repeats of length c, and n is the number of atoms in the spacer molecule not included in the repeats and wherein mc+n generally ranges from about 1 to about $100_n$; said tag oligonucleotide further comprising a complementary oligonucleotide (α-tag) annealed to the tag oligonucleotide to provide a method of measurement of conjugation success a; said T further comprising a bridging oligonucleotide having a nucleotide sequence reverse complementary to the 3' overhang nucleotide sequence of the tag oligonucleotide and a further nucleotide sequence complementary to a nucleotide sequence on the 5' end of a target nucleic acid molecule;

wherein T may be represented p times on the solid support wherein p is from about 1 to about 100,000.

Still another aspect of the present invention contemplates a method for immobilizing a target nucleic acid molecule to a partially double-stranded tag oligonucleotide anchored to a solid support, said method comprising ligating a phosphorylated 5' end of the target nucleic acid molecule to a complementary single-stranded portion of the tag oligonucleotide under conditions to permit ligase-mediated covalent bond formation wherein said tag oligonucleotide is covalently anchored to the solid support via covalent bond formation between a first chemical moiety on the surface of the solid support and a chemical moiety conjugated to the tag oligonucleotide via a molecule of structure mc+n as defined above and wherein the tag oligonucleotide is rendered partially double-stranded by annealing a complementary oligonucleotide to the tag oligonucleotide leaving a single-stranded 3' terminal portion of the tag oligonucleotide which is used to capture the target nucleic acid molecule via a bridging oligonucleotide.

The present invention further provides a kit useful in capturing and/or anchoring target nucleic acid molecules. The kit is conveniently in multi-compartment form wherein a first compartment comprises a solid support such as microspheres or microchips having a surface chemical moiety. A second compartment comprises a tag oligonucleotide having a chemical moiety capable of covalent bond formation with the surface chemical moiety of the solid support and wherein the chemical moiety on the tag is linked to the tag via a molecule of the mc+n structure as defined above. A third compartment comprises a labeled complementary tag oligonucleotide and a fourth compartment comprises a bridging oligonucleotide.

In an alternative, the kit may comprise a solid support having a partially double-stranded tag oligonucleotide anchored thereto comprising a single-stranded 3' end portion. The kit may then have a bridging oligonucleotide already attached to the single-stranded portion of the tag oligonucleotide or this may be maintained separately. A target nucleic acid molecule is then ligated to the tag oligonucleotide via the bridge oligonucleotide.

The anchoring system of the present invention has many uses such as in deconvolution of complex mixtures of nucleic acid molecules, sorting of nucleic acid molecules and for generation of microarrays, suspension arrays and optical fiber arrays.

The system may also be adopted to facilitating in vitro transcription and/or translation and the transcription and/or translation products assayed or used to screen for ligand or binding partners.

The anchoring system of the present invention may be fully or partially automated and may be used for high throughput screening of target nucleic acid molecules.

The present invention is further described by the following non-limiting Examples.

Example 1

Selection of Components of Anchoring Systems

1. Solid Support

The physicochemical structure of the surface of the solid support is an important consideration for the choice of chemical reactive moiety of the DNA to exploit for covalent attachment. The main attributes of the surface are:—
(a) ease of manipulation;
(b) inexpensive;
(c) stable in extremes of temperatures; and
(d) stable in both aqueous and organic solvents.

Suitable surfaces include glass slides for solid microarrays and silica and methacrylate microspheres for use in suspension arrays, optical fiber arrays, or micromachined devices. The one favoured at the moment and representing the most common conjugation chemistry involves a thiolated surface is exemplified below.

2. A Universal Tag for Initial Modification of the Surface

In the present system, a reactive end (amine, thiol or acryl group) is used at the 5' end of the DNA oligonucleotide. In the example given here, the 5' reactive group is an acryl, followed by two —$(OCH_2CH_2)_6$ spacers. These additions are made at point of synthesis.

To this common 5' end architecture is added a 20 base linker designed on the T7, T3, or SP6 RNA polymerase promoters along with an additional 18 bases comprising transcription and translation start signals.

The universal tag comprises the structure:—

```
                                              [SEQ ID NO: 1]
5'-Acrydite-C18-C18-TAATACGACTCACTATAGGGCGA
```

3. A Labeled αα-Tag

To assay the successful covalent attachment of the tag to the surface, a labeled reverse complementary 16-mer built to bind to the first 16 bases of the tag is used. The 3' end is fluoresceinated with 6-FAM and the 5' end is phosphorylated.

The sequence of the complementary tag is as follows:—

```
5'PO4-ATAGTGAGTCGTATTA-FAM      [SEQ ID NO: 2]
```

4. A Bridge Oligo

This bridge is built to be complementary to the last six bases of the tag as well as the first five bases of the target. It is kept small for easy removal from reactions, but long enough to be easily scored by electrophoresis. The bridge needs no 5' modifications.

Its structure is:—

```
    5'-TCCCGCTCCTAGA          [SEQ ID NO: 3]
```

5. Phosphorylated Target

This DNA is made to be specific for each experiment. It has its initial five bases reverse complementary to the five 5' bases of the bridge. The 5' end of the target is phosphorylated. The five bases of the target which hybridise to the 5' end of the bridge are sufficient to enable ligation, but not sufficient enough to significantly add to cross-hybridization. In the present system test, the 3' end of the target contained the reverse complement of the SP6 RNA polymerase promoter allowing for either translation or, in concert with T7 promoter, PCR amplification.

An example of a target is as follows:

```
                                              [SEQ ID NO: 4]
5'-PO4-GGATCTGACACGGACTGATGAATTCC-α-sp6-3'
```

Example 2

System Set-Up

1. Tag is Conjugated to Surface

The execution of this step depends on the chemistry and surface used. The assay for measurement of amount of covalent binding is performed by binding α-tag to the solid surface. Amount of fluorescence at 521 nm is measured after excitation by a high-energy light source. The argon ion laser of the ABI 377, ABI 3700 or BD FacsCalibur may conveniently be used to measure this quantity.

2. Target is Ligated to Tag by Bridging Ligation

The bridge and target are added in equimolar amounts to the tag-modified surface with T4 DNA ligase. Successful ligation of target to tag is measured indirectly by measuring the ligation of α-tag to bridge electrophoretically (a 27-mer vs an 11-mer and a 16-mer) or by measuring the binding of OLIGREEN, a single stranded fluorescent binding dye from Molecular Probes. By measuring the amount of binding to the surface before and after ligation, it is easy to quantify the amount of ssDNA gained by the ligation-anchoring step.

Example 3

Universal Primed Target Production

The primary aim of this Example is to introduce a high efficiency, low cost, easily used microsphere based system for capturing nucleic acid molecules. The present system is useful for specific testing of reagents which can be used in conjunction with a flow cytometer or other bead based instrument.

The system may also be used for generation of capture reagents for combinatorial screening as well as a system for solid phase PCR and/or single-stranded extensions.

The three component linker used to modify a thiolated solid phase is shown in FIG. 1.

Figure 2:
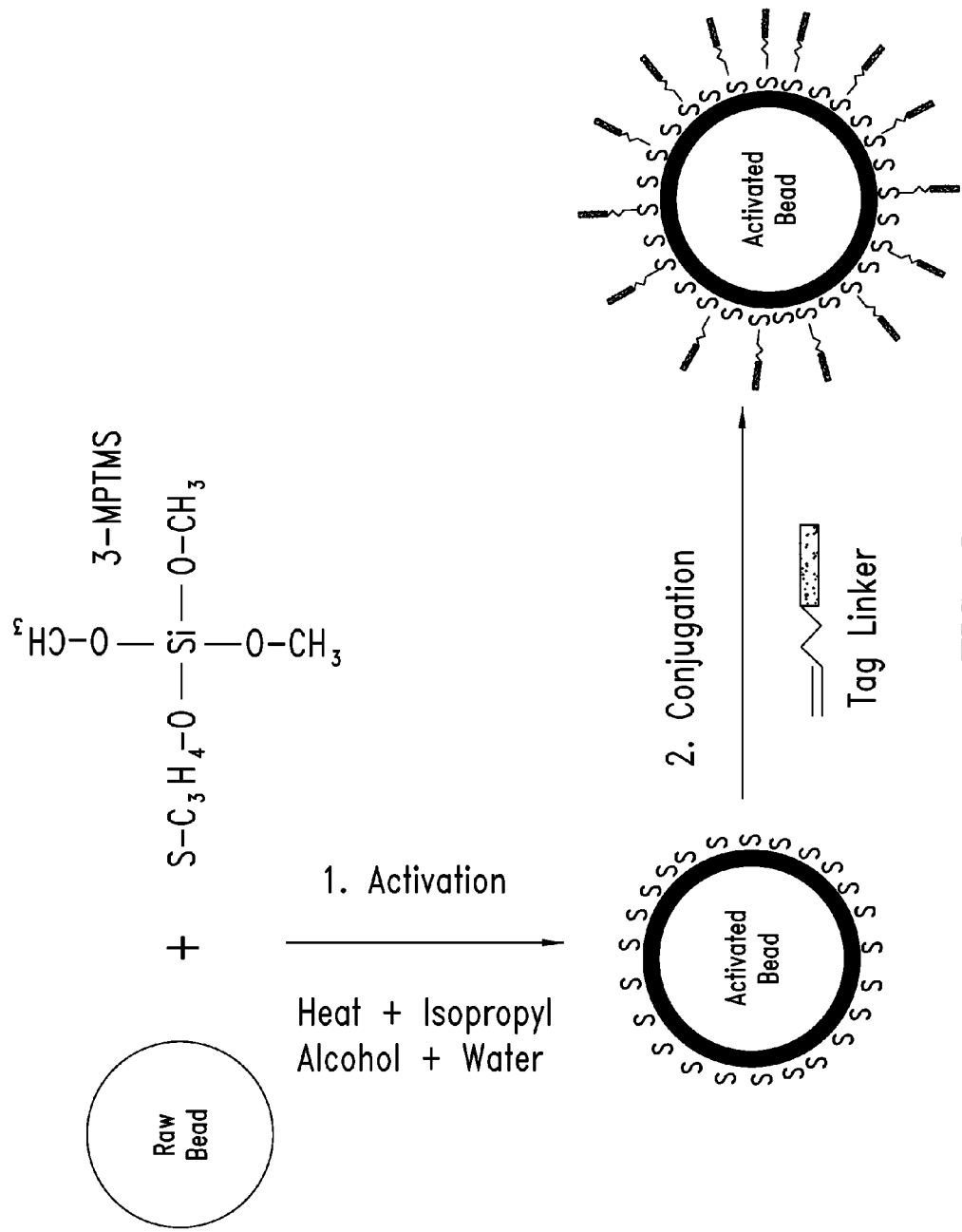
FIG. 2 is a representation of the process of two-step bead activation with silane to produce a surface with a high density of exposed thiol groups to create a tagged microsphere. Step (1): Raw silica beads are reacted with sulfur containing silane (3-Mercaptoprophyl trimethoxysilane ($HS-CH_2-CH_2-CH_2-Si(Ome_3)$)). Step (2): Activated beads with dense blanket of surface thiols are reacted with Tag linker (see FIG. 1) to produce a bead with many thousands of covalently bound uni-directionally tethered DNA molecules.

A Universal Forward Oligo (UF) is then generated and in one example comprises the SP6 RNA polymerase promoter with a 5' acrydite, a 30-atom spacer, followed by the sequence. This is conjugated to form a bead: UF complex (FIG. 2).

The efficiency of conjugation is measured by measuring the binding of α-UFO which is a phosphorylated, internally labeled complement to the first 13 bases of the UFO.

The resulting bead has a configuration shown in FIG. 3.

Successfully conjugated bead preps are made in bulk, $5 \times 10^{10}$ beads (usually $5 \times 10^6$ beads/ul, so $5 \times 10^9$ beads/ml=about 10 ml of bead stock).

Specific targets are produced by a two step ligation protocol in which a Universal Bridging Oligo (UBO) is first bound to the 5' end of each target and then the resulting "sticky-ended" target is ligated to the bead: UFO:α-UFO defined as above.

Figure 4:
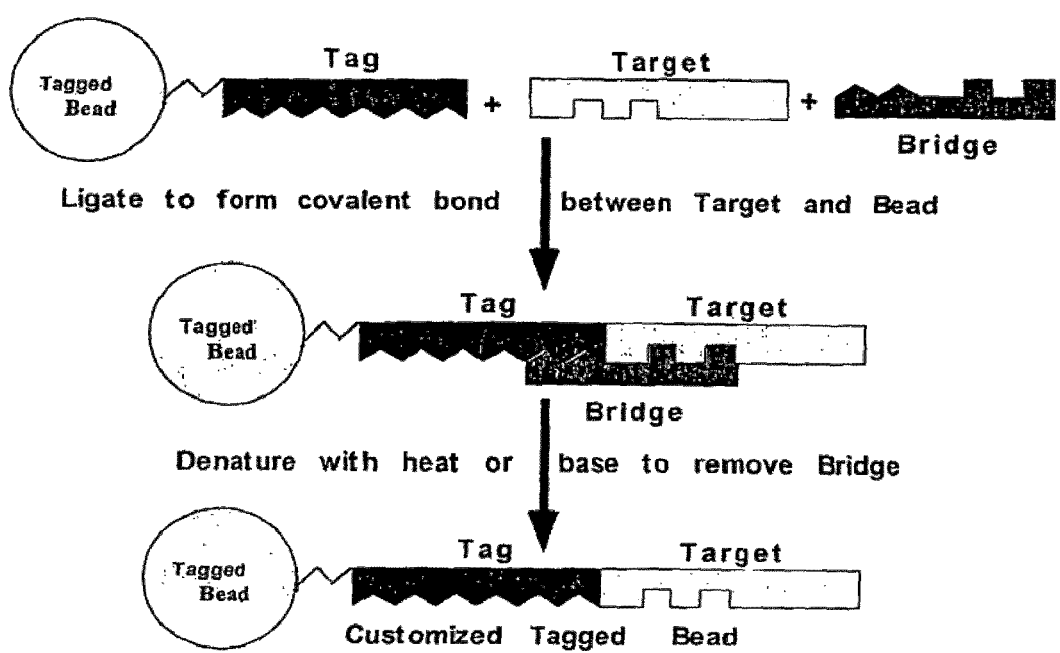
FIG. 4 is a diagrammatic representation showing ligase-mediated customization Phosphorylated target DNA and bridge DNA is mixed with tagged microspheres, T4 DNA ligase, and ATP. After brief reaction at room temperature, bridge and unincorporated targets are removed by heat and separation from the microspheres.

The UBO has the following characteristics. The first six bases 5' will be complementary to the last six bases of the UFO and the final five bases will be random. The resulting complex is shown in FIG. 4.

Thus, a small (e.g. 1024) library is created. The key to this system working is the randomness of this library as well as the workable size. The size of this variable domain is kept at five to be both manageable as well as easily removed by gel filtration at the end of the first hybridization step.

The target DNA is synthesized with a 5' phosphate, a number of bases specific to the experiment, and a terminal 17 bases complementary to the T3 RNA polymerase promoter. As an example, a target of sequence GCAACCATTATC [SEQ ID NO:5] is synthesized with a 5' $PO_4$ and a terminal T3 polymerase signal sequence of TCCCTTTAGTGAGGGTT [SEQ ID NO:6] for the following final construct:

[SEQ ID NO: 7]

To assess the efficiency of the ligation, the relative amounts of bound 13-mer and 24-mer would be ascertained by quantitative capillary electrophoresis on an ABI 3700 analyzed with Genescan software. Populations of particles from successful ligations would be sorted by flow cytometry.

Example 4

Ligase-Mediated Customization

Phosphorylated target DNA and bridge DNA is mixed with tagged microspheres, T4 DNA ligase, and ATP. After brief reaction at room temperature, bridge and unincorporated targets are removed by heat and separation from the microspheres. A diagram of ligase-mediated customization is shown in FIG. 4.

Example 5

Ligation-Mediated Customization Efficiency

Figure 5:
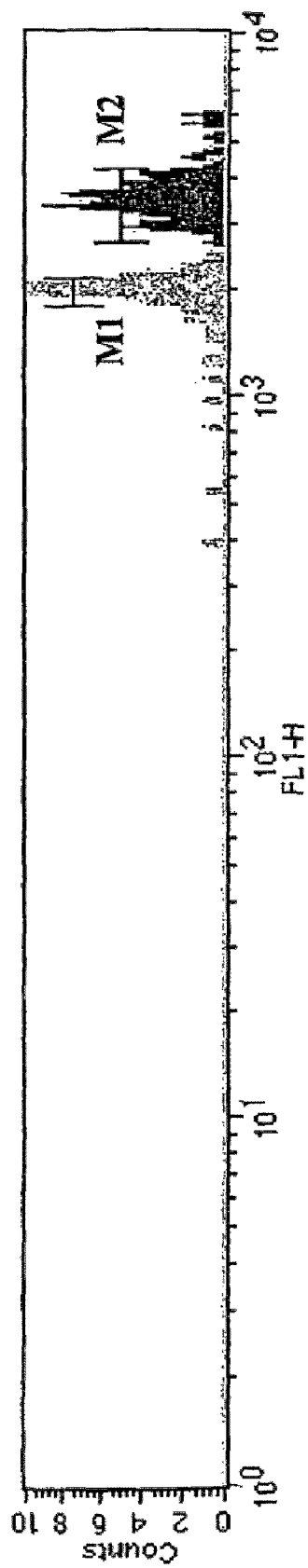
FIG. 5 is a graphical representation showing testing of ligation efficiency by the use of OLIGREEN (registered trademark). Customized beads (Tag+Target; M2 or left-most peak) and tagged beads (Tag only/no target; M1 or right-most peak) were stained with a small amount of OLIGREEN (registered trademark). Beads were run on Becton Dickinson FacsCalibur flow cytometer. Ligation efficiency is measured by testing the ratio of M2 (tagged+target)/M1 (tag only). For this example, M2/M1 is approximately 2.5, indicative of a successful ligation. M2/M1 values of <1.7 generally represent ligation efficiency of less than 80% of target DNA modified.

Customized beads (tag+target; M1 or left-most peak of FIG. 5) and tagged beads (Tag only/no target; M2 or right-most peak) were stained with a small amount of OLIGREEN (registered trademark). Beads were run on Becton Dickinson FacsCalibur flow cytometer. Ligation efficiency is measured by testing the ratio of M2 (tagged+target)/M1 (tag only). For this Example, M2/M1 is approximately 2.5, indicative of a successful ligation. M2/M1 values of <1.7 generally represent ligation efficiency of less than 80% of target DNA modified. The results are shown in FIG. 5.

Example 6

Figure 6A:
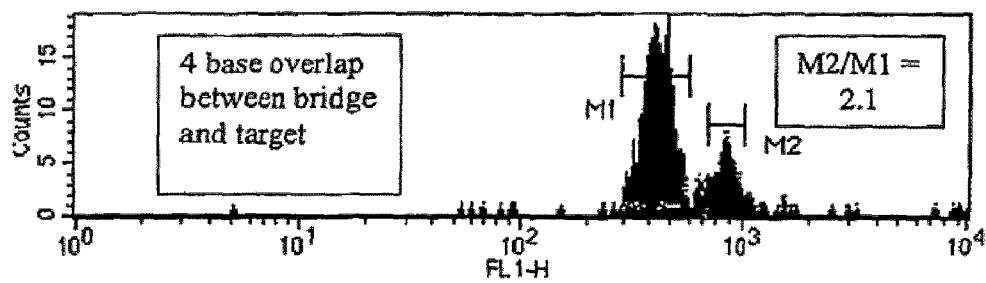
FIG. 6 is a graphical representation of optimal overhang length for ligase-mediated conjugation to tagged microspheres. Bridge oligonucleotides differing by only the number of 5' bases in direct base pairing with target were tested by OLIGREEN (registered trademark) ligation assay (see FIG. 5). (A) 4 base pair overlap; (B) five base pair overlap; (C) six base pair overlap. M1 or Marker 1 is the mean fluorescence of the tagged microsphere. M2 is the mean fluorescence of the tagged microsphere post ligation of target. The quantity M2/M1 measures the relative gain in fluorescence and thus the amount of bound DNA. In this example, five and six base overlaps have greater ligation efficiency than four base overlap.
Figure 6B:
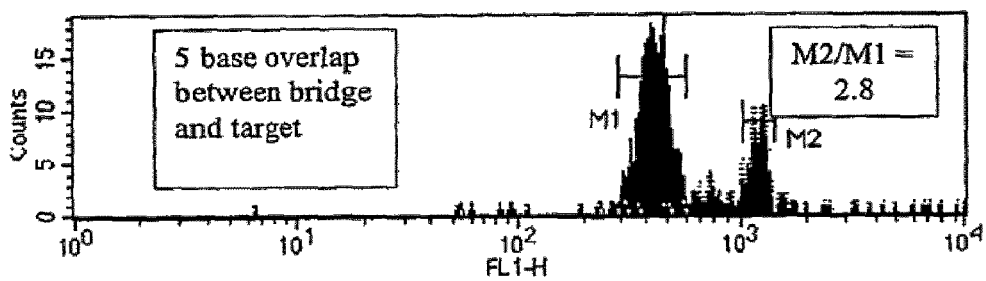
Figure 6C:
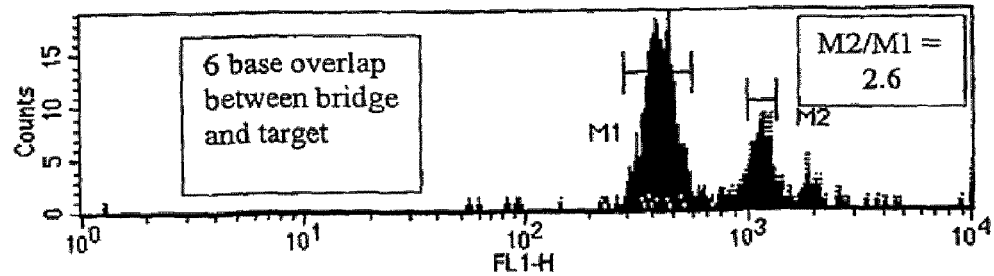

Test of Optimal Overhang Length for Ligase-Mediated Conjugation to Tagged Microspheres Bridge oligonucleotides differing by only the number of 5' bases in direct base pairing with target were tested by OLI-GREEN (registered trademark) ligation assay (see FIG. 6). In this Figure, M1 or Marker 1 is the mean fluorescence of the tagged microsphere. M2 is the mean fluorescence of the tagged microsphere post-ligation of target. The quantity M2/M1 measures the relative gain in fluorescence and thus the amount of bound DNA. In this Example, five and six base overlaps have greater ligation efficiency than four base overlap. The results are shown in FIG. 6.

Example 7

Figure 7A:
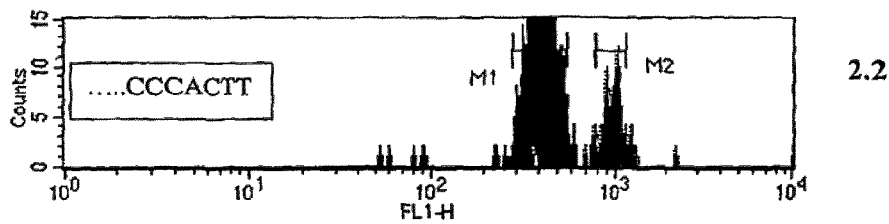
FIG. 7A represents the unsubstituted bridge.
Figure 7B:
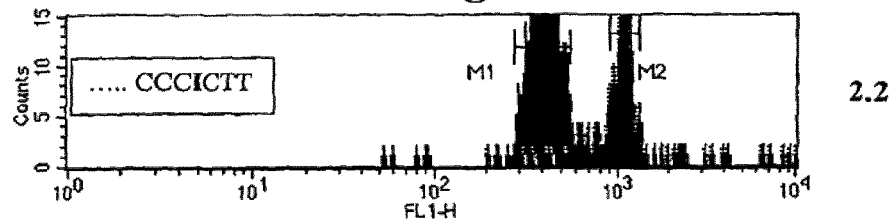
FIGS. 7B-E represent increasing numbers of inosines in the bridges. A box in the left side of each figure gives the tested sequence of the 5' overhang. In each experiment, $1 \times 10^5$ beads with immobilized tags were reacted with 2.0 nMols of target oligonucleotide and appropriate bridge as well as 20 units T4 DNA ligase, 1 mM ATP, 10 mM $MgCl_2$. Reactions were carried out at room temperature for 15 minutes. Unligated DNAs were removed by two 0.2 M NaOH washes. Beads with ligase mediated conjugated products were assayed by OLIGREEN (registered trademark) binding assay using Becton Dickinson FacsCalibur. Ligation efficiency is calculated as the sample fluorescence post binding (M2) divided by the control mean fluorescence (M1). At least 200 events for each data point were collected.
Figure 7C:
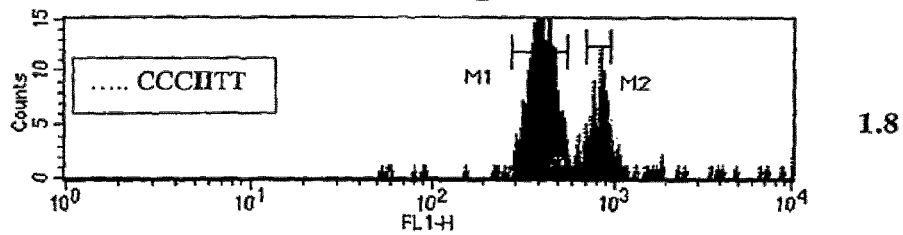
Figure 7D:
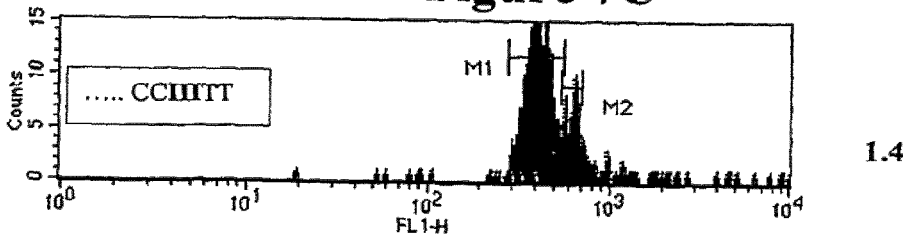
Figure 7E:
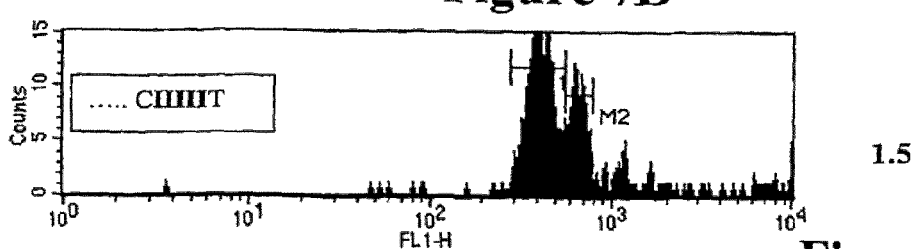
Figure 8A:
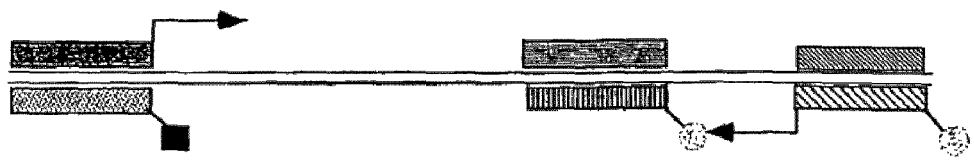
FIG. 8 is a diagrammatic representation showing use of ligase-mediated customized silica microspheres in solid phase PCR. This experiment is divided into three sections. (A) description of the regions of the DNA to be amplified with labeled probes and their targets; (B) Controls to assess pre-PCR presence of immobilized sequences; (C) Post-PCR probes of amplified sequences.
Figure 8A:
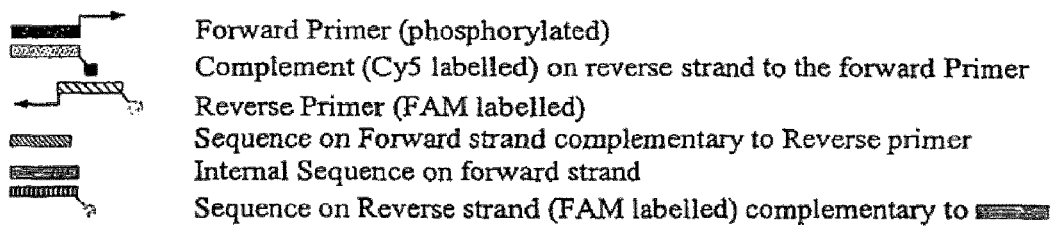
Figure 8B:
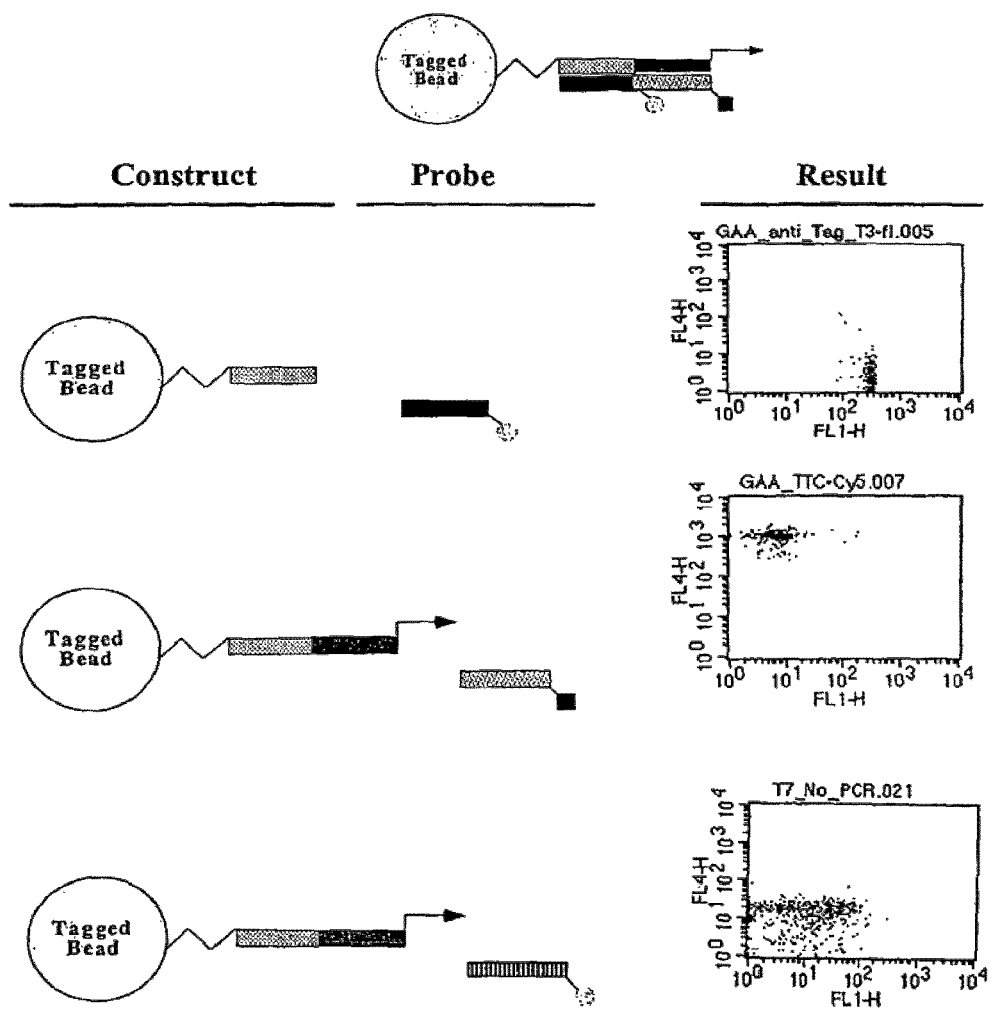
Figure 8C:
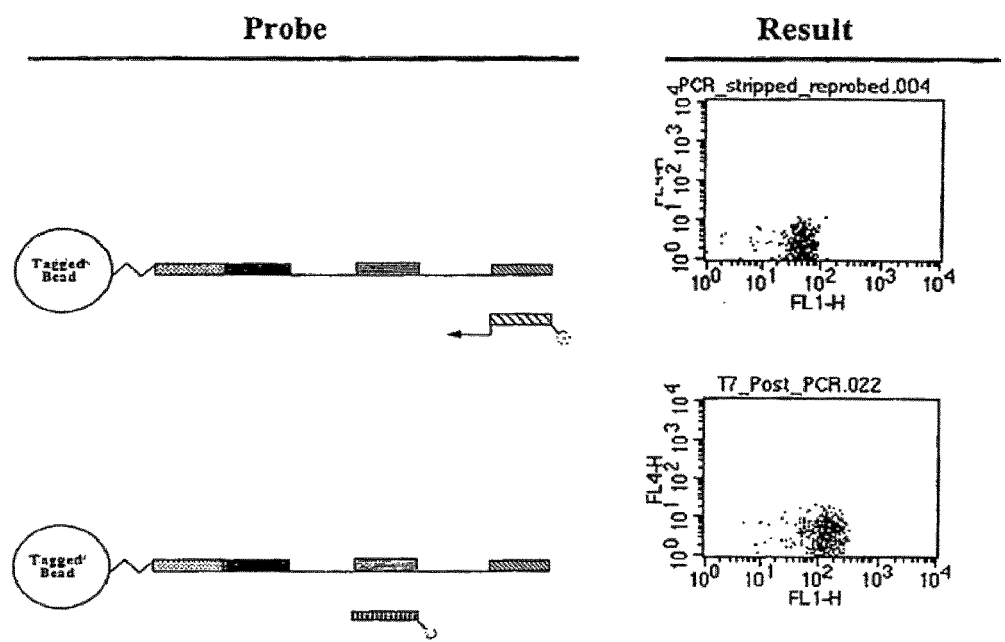

Universal Binding Analogs for General Use Bridges in Ligation-Mediated Conjugation of Tagged Microspheres All bridges had a common sequence of 5'-CXXXXXT [SEQ ID NO:8] CAT AGC TGT CCT-3' [SEQ ID NO:9]. The 3' italicized 12 bases were common to all bridges and hybridized to the 3' 12 bases of the immobilized tag. The underlined sequence CXXXXXT [SEQ ID NO:8} represents the variable 5' overhang which hybridized to the target sequence. The Xs represent nucleotide positions which were variable in this test between the actual base and inosines, which are general binding base analogs. FIG. 7A represents the substituted bridge. FIGS. 7B-E represent increasing numbers of inosines in the bridges. A box in the left side of each figure gives the tested sequence of the 5' overhang. In each experiment, $1 \times 10^5$ beads with immobilized tags were reacted with 2.0 nMols of target oligonucleotide and appropriate bridge as well as 20 units T4 DNA ligase, 1 mM ATP, 10 mM $MgCl_2$. Reactions were carried out at room temperature for 15 minutes. Unligated DNAs were removed by two 0.2 M NaOH washes. Beads with ligase mediated conjugated products were assayed by OLIGREEN (registered trademark) binding assay using Becton Dickinson FacsCalibur. Ligation efficiency is calculated as the sample fluorescence post binding (M2) divided by the control mean fluorescence (M1). At least 200 events for each data point were collected. The results are shown in FIG. 7.

Example 8

Use of Ligase-Mediated Customized Silica Microspheres in Solid Phase PCR

This Experiment is divided into three sections. (A) A 187 by DNA fragment generated by PCR with the following landmarks. (B) A tagged microsphere is customized with the phosphorylated forward primer. The FAM labeled α-tag probe as well as the Cy5 complement to the target are used to assess the efficiency of the conjugation. Background levels of binding are determined for all labeled probes. (C) PCR is performed using immobilized forward primer. Success is determined by stripping non-covalently bound strand and reprobing with either the original reverse primer or the internally labeled complement. The results are shown in FIG. 8.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

SEQUENCE LISTING

<160> NUMBER OF SEQ ID NOS: 11

<210> SEQ ID NO 1
<211> LENGTH: 23
<212> TYPE: DNA
<213> ORGANISM: artificial sequence
<220> FEATURE:
<223> OTHER INFORMATION: 5' acrydite universal tag

<400> SEQUENCE: 1
taatacgact cactataggg cga                                        23

<210> SEQ ID NO 2
<211> LENGTH: 16
<212> TYPE: DNA
<213> ORGANISM: artificial sequence
<220> FEATURE:
<223> OTHER INFORMATION: PO4 complementary tag

<400> SEQUENCE: 2
atagtgagtc gtatta                                                16

<210> SEQ ID NO 3
<211> LENGTH: 13
<212> TYPE: DNA
<213> ORGANISM: artificial sequence
<220> FEATURE:
<223> OTHER INFORMATION: bridge oligonucleotide

<400> SEQUENCE: 3
tcccgctcct aga                                                   13

<210> SEQ ID NO 4
<211> LENGTH: 26
<212> TYPE: DNA
<213> ORGANISM: artificial sequence
<220> FEATURE:
<223> OTHER INFORMATION: PO4 target

<400> SEQUENCE: 4
ggatctgaca cggactgatg aattcc                                     26

<210> SEQ ID NO 5
<211> LENGTH: 12
<212> TYPE: DNA
<213> ORGANISM: artificial sequence
<220> FEATURE:
<223> OTHER INFORMATION: target synthesized with 5' PO4

<400> SEQUENCE: 5
gcaaccatta tc                                                    12

<210> SEQ ID NO 6
<211> LENGTH: 17
<212> TYPE: DNA
<213> ORGANISM: artificial sequence
<220> FEATURE:
<223> OTHER INFORMATION: terminal T3 polymerase signal sequence

<400> SEQUENCE: 6
tccctttagt gagggtt                                               17

```
<210> SEQ ID NO 7
<211> LENGTH: 29
<212> TYPE: DNA
<213> ORGANISM: artificial sequence
<220> FEATURE:
<223> OTHER INFORMATION: a target DNA sequence

<400> SEQUENCE: 7
gcaaccatta tctcccttta gtgagggtt                                    29

<210> SEQ ID NO 8
<211> LENGTH: 7
<212> TYPE: DNA
<213> ORGANISM: artificial sequence
<220> FEATURE:
<223> OTHER INFORMATION: 5' overhang of common sequence of bridge
<220> FEATURE:
<221> NAME/KEY: misc_feature
<222> LOCATION: (2)..(6)
<223> OTHER INFORMATION: N = X

<400> SEQUENCE: 8 cnnnnnt                                                             7

<210> SEQ ID NO 9
<211> LENGTH: 12
<212> TYPE: DNA
<213> ORGANISM: artificial sequence
<220> FEATURE:
<223> OTHER INFORMATION: a common sequence of bridge

<400> SEQUENCE: 9
catagctgtc ct                                                      12

Figure 3C:
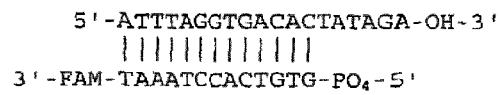
FIG. 3 is a diagrammatic representation showing testing of conjugation efficiency. (A) Immobilized tag sequence; (B) α-tag: reverse complement to tag with 3' FAM label; (C) approx. $10^4$ untreated silica microspheres probed with 10 pMol α-tag; (D) approx. $10^4$ activated beads probed with 10 pMol α-tag; (E) approx. $10^4$ beads with immobilized Tags probed with 10 pMol α-tag. Fluorescence calculated on Becton-Dickinson FacsCalibur.
Figure 3C:
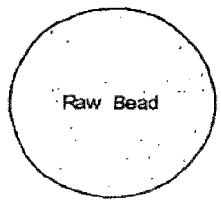
Figure 3C:
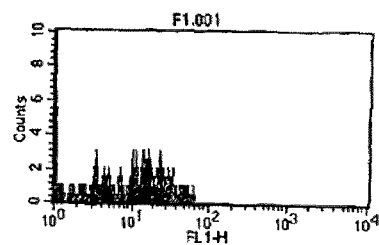
Figure 3D:
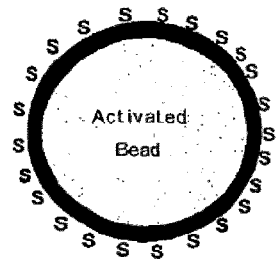
Figure 3D:
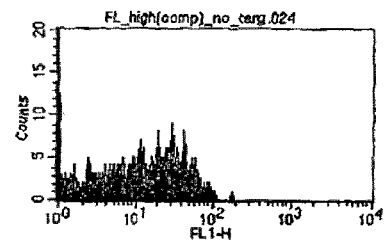
Figure 3E:
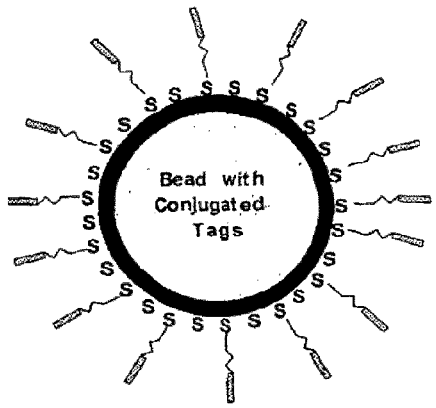
Figure 3E:
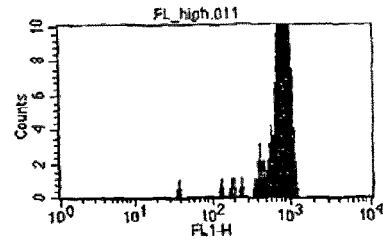

<210> SEQ ID NO 10
<211> LENGTH: 19
<212> TYPE: DNA
<213> ORGANISM: artificial sequence
<220> FEATURE:
<223> OTHER INFORMATION: a tag sequence (Figure 3A)

<400> SEQUENCE: 10
atttaggtga cactataga                                               19

<210> SEQ ID NO 11
<211> LENGTH: 13
<212> TYPE: DNA
<213> ORGANISM: artificial sequence
<220> FEATURE:
<223> OTHER INFORMATION: an alpha-tag sequence (Figure 3B)

<400> SEQUENCE: 11
gtgtcaccta aat                                                     13
```

The invention claimed is:

1. A universal nucleic acid anchoring system comprising a surface first chemical moiety which participates in covalent carboxyl bond formation with a second chemical moiety conjugated to a tag oligonucleotide rendered partially double-stranded by annealing an α-tag to the tag oligonucleotide to provide a 3' overhang portion of the tag oligonucleotide, wherein the tag oligonucleotide is employed as a substrate for ligase mediated covalent bonding to a single-stranded target nucleic acid molecule, such that the single-stranded target nucleic acid molecule is ligated to the tag oligonucleotide, wherein the tag oligonucleotide comprises the second chemical moiety conjugated to a known oligonucleotide sequence via a molecule having the structure mc+n atoms, from about 1 to about 100, wherein m is the number of repeats, c is the number of atoms in each repeat, and n is the number of atoms not in the repeats.

2. The universal nucleic acid anchoring system of claim 1, comprising a solid support in the form of a microsphere, microchip or a glass, plastic or ceramic slide.

3. The universal nucleic acid anchoring system of claim 2, wherein the solid support is a microsphere.

4. The universal nucleic acid anchoring system of claim 1, wherein the covalent carboxyl bond is formed with an amine group, a thiol group or an acryl group on the secondary chemical moiety.

5. The universal nucleic acid anchoring system of claim 1, wherein the second chemical moiety is an amine group.

6. The universal nucleic acid anchoring system of claim 1, wherein the α-tag oligonucleotide is labeled with a reporter molecule and is phosphorylated at its 5' end.

7. The universal nucleic acid anchoring system of claim 1, comprising a bridging oligonucleotide, said bridging oligonucleotide having a nucleotide sequence complementary to the nucleotide sequence of the 3' overhang portion of the tag oligonucleotide and a nucleotide sequence complementary to a terminal end portion of the target nucleic acid molecule.

8. The solid phase of claim 7, comprising a target nucleic acid molecule in ligase-mediated covalent bonding to the tag oligonucleotide molecule anchored to the solid phase.

9. The solid phase of claim 6, further comprising a bridging oligonucleotide, said bridging oligonucleotide having a nucleotide sequence complementary to the nucleotide sequence of the 3' overhang portion of the tag oligonucleotide and a nucleotide sequence complementary to a terminal end portion of the target nucleic acid molecule.

* * * * *